(12) United States Patent
Mikoshiba et al.

(10) Patent No.: US 7,709,441 B2
(45) Date of Patent: May 4, 2010

(54) CONTROL OF FUNCTION OF INTRACELLULAR CA ION

(75) Inventors: Katsuhiko Mikoshiba, Tokyo (JP); Junji Hirota, Osaka (JP); Hideaki Ando, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 188 days.

(21) Appl. No.: 11/811,588

(22) Filed: Jun. 11, 2007

(65) Prior Publication Data

US 2008/0064082 A1 Mar. 13, 2008

Related U.S. Application Data

(60) Division of application No. 11/283,193, filed on Nov. 18, 2005, now Pat. No. 7,276,582, which is a continuation of application No. PCT/JP03/14004, filed on Oct. 31, 2003.

(30) Foreign Application Priority Data

May 19, 2003 (JP) ............................. 2003-141083

(51) Int. Cl.
*A61K 8/66* (2006.01)
*A61K 38/00* (2006.01)

(52) U.S. Cl. ....................... 514/2; 530/388.22; 530/350

(58) Field of Classification Search ....................... None
See application file for complete search history.

(56) References Cited

U.S. PATENT DOCUMENTS 7,056,692 B2 * 6/2006 Deuel ........................... 435/21
2003/0108547 A1 * 6/2003 Jakobsen ................. 424/144.1

FOREIGN PATENT DOCUMENTS

EP 0 992 587 A2 4/2000

OTHER PUBLICATIONS

Nishimori et al. (2001) Carbonic anhydrase isozymes in the human pancreas, Dig. Liver Dis., vol. 33, No. 1, pp. 68-74.*
Mori et al. (1999) Isolation and characterization of CA XIV, a novel membrane-bound carbonic anhydrase from mouse kidney, J. Biol. Chem., vol. 274, No. 22, pp. 15701-15705.*
Scozzafava et al. (200)4) Modulation of carbonic anhydrase activity and its applications in therapy, Expert Opin. Ther. Patens, vol. 14, No. 5, pp. 667-702.*
Sjoblom et al. (1996) Two point mutations convert a catalytically inactive carbonic anhydrase-related protein (CARP) to an active enzyme, FEBS Lett., vol. 398, pp. 322-325.*
A. Uji et al., "Molecules interacting with PRIP-2, a novel Ins (1,4,5)P₃ binding protein type 2: Comparison with PRIP-1" *Life Sciences*, 72:443-453 (2002).

H. Ando et al., "IRBIT, a Novel Inositol 1,4,5-Trisphosphate (IP3) Receptor-binding Protein, Is Released from the IP₃ Receptor upon IP₃ Binding to the Receptor", *The Journal of Biological Chemistry*, 278(12):10602-10612 (2003).
K. Taniuchi et al., "cDNA cloning and develpmental expression of murine carbonic arihydrase-related proteins VIII, X, and XI", *Molecular Brain Research*, 109:207-215 2002.
N. Okamoto et al., "cDNA sequence of human carbonic anhydrase-related protein, CA-RP X: mRNA expressions of CA-RP X and XI in human brain", *Biochimica et Biophysica Acta*, 1518:311-316 (2001).
I. Bosanac et al, "Structure of the inositol 1,4,5-trisphosphate receptor binding core in complex with its ligand", *Nature*, 420(6916):696-700, Epub (2002).
Bataller et al., "Carbonic anhydrase-related protein VIII: autoantigen in paraneoplastic cerebellar degeneration", Ann. Neurol. vol. 56, No. 4, pp. 575-579 (2004).
Supuran et al., "Carbonic anhydrase inhibitors in the treatment and prophylaxis of obesity", Expert Opin. Ther. Patents, vol. 13, No. 10, pp. 1545-1550 (2003).
Hirota et al., "Carbonic anhydrase-related protein is a novel binding protein for inositol 1,4,5-trisphosohate receptor type 1", Biochem. J. vol. 372, Part 2, pp. 435-441 (2003).
Elleby et al., "Enhancement of catalytic efficiency by the combination of the site-specific mutations in a carbonic anhydrase-related protein", Eur. J. Biochem. vol. 267, No. 19, pp. 5908-5915 (2000).
NCBI Sequence Viewer (Accession No. 1677117A, updated 2006) http://www.ncbi.nlm.gov/entrev/viewer.fcgi?db=protein&val=30581041, pp. 1-2.
NCBI Sequence Viewer (Accession No. 35653, updated 2006) http://www.ncbi.nlm.nih.gov/entrez/vieer.fcgi?db=nucleotide&val=5069431, pp. 1-2.
NCBI Sequence Viewer (Accession No. P28651, updated 2006) http://www.ncbi.nlm.gov/entrev/viewer.fcgi?db=protein&val=30581041, pp. 1-4.
Ando et al., "Identification of 60kDa molecule which binds to IP3 receptor and dissociates therefrom by IP3," Seikagaku (2002), 74(8):760 (*full translation included*).

* cited by examiner

*Primary Examiner*—Anand U Desai
*Assistant Examiner*—Samuel Liu
(74) *Attorney, Agent, or Firm*—Peter F. Corless; Christine C. O'Day; Edwards Angell Palmer & Dodge LLP

(57) ABSTRACT

Analysis of substance capable of binding with inositol-1,4,5-triphosphate (IP₃) receptor (IP₃R), preferably with a regulation domain of IP₃R; analysis of the function of IP₃R; and establishing of a method of treatment or diagnosis for various malfunctions and diseases associated with IP₃R. In particular, control of the activity of intracellular $Ca^{2+}$ release. More specifically, a regulator for the activity of inositol-1,4,5-triphosphate (IP₃) receptor (IP₃R), comprised of carbonic anhydrase related protein (CARP); a control agent for intracellular calcium release, comprised of carbonic anhydrase related protein (CARP); and a method of control therewith.

4 Claims, 6 Drawing Sheets

Fig. 5
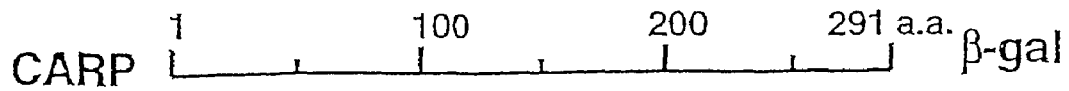
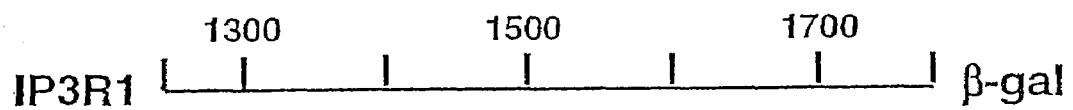

CONTROL OF FUNCTION OF INTRACELLULAR CA ION

TECHNICAL FIELD

The present invention relates to control of the function of intracellular $Ca^{2+}$ release. More particularly, the present invention relates to a regulator for the activity of inositol-1,4,5-triphosphate ($IP_3$) receptor ($IP_3R$) comprising carbonic anhydrase-related protein (CARP), a control agent for intracellular calcium release comprising carbonic anhydrase-related protein (CARP), and a method of control therewith.

BACKGROUND ART

Lipids have been shown to have important roles in an intracellular signal transmission system. In particular, researches on signal transmission by phosphates of phosphatidylinositol are actively conducted.

Phosphatidylinositol (PI) is a substance that inositol is bound as a phosphate ester to a remaining hydroxyl group of diacylglycerol. Phosphatidylinositol (PI) is one kind of phospholipids that is found on membranes of cells, however it occupies less than 10% of the total phospholipids. Phosphatidylinositol (PI) plays two major roles. First, it remains on the membrane and serves as a scaffold for a variety of phosphorylation reactions for a phosphorylated enzyme and the like. Second, it serves to release phosphorylated inositol as a second messenger upon hydrolysis of the phosphorylated inositol moiety.

Hydroxyl groups in the inositol moiety of PI may further be phosphorylated, and inositol phospholipids in which 3-position, 4-position or 5-position or two or more of these positions is/are phosphorylated are also known. In particular, phosphatidylinositol 4,5-bisphosphate ($PI(4,5)P_2$) in which 4-position and 5-position are phosphorylated not only forms an intermediate of phosphatidylinositol 3,4,5-triphosphate ($PI(3,4,5)P_3$) that plays a role in vesicular transport and signal transmission to a nucleus, but also plays an important role by itself.

$PI(4,5)P_2$ is able to bind to a variety of actin binding proteins, and serves to keep and change the shape of a cell by allowing rearrangement of actin in the cell. Another important role of the $PI(4,5)P_2$ is that it is hydrolyzed by phospholipase C (PLC) into inositol-1,4,5-triphosphate ($IP_3$) and diacylglycerol (DAG) which are then released as second messengers. The released inositol-1,4,5-triphosphate (IP3) binds to an $IP_3$ receptor ($IP_3R$) residing on the surface of an endoplasmic reticulum of a cell and release $Ca^{2+}$ stored in endoplasmic reticula into the cytoplasm, thereby activating a variety of $Ca^{2+}$ dependent enzymes. DAG also activates C kinase.

Upon binding of substances such as hormones, cytokines and neurotransmitters on receptors of a cell, production of inositol-1,4,5-triphosphate ($IP_3$) is induced in the cell, and the $IP_3$ binds to inositol-1,4,5-triphosphate ($IP_3$) receptor ($IP_3R$) residing on the surface of endoplasmic reticula of the cell. The $IP_3R$ converts $IP_3$ signaling into $Ca^{2+}$ signaling, and thus plays crucial roles in a wide range of cellular functions such as embryonic development, differentiation of cells, proliferation, phagocytosis, granule secretion, motion and actions in nerve system, and it is especially important for the $IP_3R$ to normally function in cells in order to keep the homeostasis of cells. Thus, $IP_3R$ is not only an important protein involved in signal transmission of cells, but also an important protein capable of regulating a variety of functions of cells. Therefore, modulation of the function of $IP_3R$ makes it possible to adjust a variety of actions in cells.

As the significance of $IP_3$ or $IP_3R$ in a cell becomes clear, researches on these proteins are conducted more actively. As such, a patent application relating to a monoclonal antibody against $IP_3R$ (See prior art document 1, Japanese Patent Application Laid-open No. 8-134099), a patent application relating to a method of competition for $IP_3$ (See prior art document 2, Japanese Translation of PCT International Application No. 8-502068) and a patent application relating to polypeptides that bind to $IP_3R$ with high affinity (see prior art document 3, Japanese Patent Application Laid-open No. 2000-135095) have been filed.

So far, molecular cloning studies have revealed that the $IP_3R$ family in mammalian consists of at least three subtypes. (see prior art documents 4 to 6, Furuichi, T., Yoshikawa, S., et al., (1989), Nature, 342, 32-38; Blondel, O., Takeda, J., et al., (1993), J. Biol. Chem., 268, 11356-11363; Yamamoto-Hino, M., Sugiyama, T., et al., (1994), Receptors Channels, 2, 9-22). Structural and functional studies have shown that $IP_3Rs$ are composed of three domains: ligand binding, modulatory, and channel (see prior art document 7, Furuichi, T., Kohda, K., et al., (1994), Curr. Opin. Neurobiol., 4, 294-303).

The binding domain which is N-terminal stretch of approximate 600 amino acids in $IP_3R$ is responsible for binding of $IP_3$. Mutational analysis showed three amino acid residues in this region, for example, Arg-265, Lys-508 and Arg-511 in mouse $IP_3R$ type 1 are critical for $IP_3$ binding, and Arg-658 is determinant for binding specificity to various inositol phosphates.

The channel domain has six membrane spanning segments, which are clustered near the C-terminus of $IP_3R$ and correspond to $Ca^{2+}$ channel. With respect of first to fourth membrane spanning domains, high homology is maintained in the $IP_3R$ family.

The modulatory domain resides between the N-terminal binding domain and the C-terminal channel domain, and the modulatory domain contains binding sites for various modulators such as $Ca^{2+}$, $Ca^{2+}$-calmodulin, FK506 binding protein 12K, ATP, and sites for phosphorylation by cAMP-dependent protein kinase, cGMP-dependent protein kinase and protein kinase C. This modulatory domain may transduce $IP_3$-binding to channel opening. $IP_3$-induced $Ca^{2+}$ release maybe regulated by various modifications in the modulatory domain. Interestingly, homology of this region among the $IP_3R$ family is low in comparison with other regions and results in different modifications between subtypes, which suggests that each type of $IP_3R/Ca^{2+}$ channel function may be differently modulated to produce unique channel properties.

Since the function of $IP_3R$ is finely adjusted by substances that bind to the modulatory domain of $IP_3R$, elucidation of substances that bind to the modulatory domain of $IP_3R$ leads to elucidation of the function of $IP_3R$, which will be very useful for therapy and diagnosis of a variety of diseases that are caused by the same.

Carbonic anhydrase-related protein (CARP) is a protein identified by screening genes specific for a Purkinje cell (a large nerve cell of cerebellar cortex, having dendrites arranged on the surface crossing a piriform cell body and flocculus) (see prior art document 8, Karo, K., (1990), FEBS Lett., 271, 137-40). CARP comprises 291 amino acids, and has an acidic amino acids cluster of 16 glutamic acid (Glu) residues and 4 aspartic acid (Asp) residues within the N-terminal 50 amino acids. CARP has a main carbonic anhydrase motif, but lacks carbonic anhydrase activity due to the absence of catalytic zinc coordinating residues. Indeed, it has been reported that CARP has no carbonic anhydrase activity.

Also the human CARP gene has been cloned (see prior art document 9, Skaggs, L. A., Bergenhem, N. C., et al., (1993), Gene, 126, 291-221), and shown to have 98% homology in amino acid residues to that of mouse, suggesting that CARP is highly conserved in the course of evolution. However, at the present stage, neither elucidation of function of CARP nor comprehensive elucidation about tissue distribution has been achieved, although it has been found that CARP is highly expressed in a Purkinje cell of cerebellum.

Prior art documents in relation to the invention of the present application are as follows.
1. Japanese Patent Application Laid-open No. 8-134099
2. Japanese Translation of PCT International Application No. 8-502068
3. Japanese Patent Application Laid-open No. 2000-135095
4. Furuichi, T., Yoshikawa, S., et al., (1989), Nature, 342, 32-38
5. Blondel, O., Takeda, J., et al., (1993), J. Biol. Chem., 268, 11356-11363
6. Yamamoto-Hino, M., Sugiyama, T., et al., (1994), Receptors Channels, 2, 9-22
7. Furuichi, T., Kohda, K., et al., (1994), Curr. Opin. Neurobiol., 4, 294-303
8. Karo, K., (1990), FEBS Lett., 271, 137-40
9. Skaggs, L. A., Bergenhem, N. C., et al., (1993), Gene, 126, 291-221
10. Bultynck G, De Smet P, et al., (2001), Biochem J., 354, 413-22

DISCLOSURE OF THE INVENTION

It is an object of the present invention to elucidate substances that bind to inositol-1,4,5-triphosphate ($IP_3$) receptor ($IP_3R$), preferably to a modulatory domain of $IP_3R$, to elucidate the function of $IP_3R$, as well as to establish a therapeutic method and a diagnosis method for various disorders and diseases in which $IP_3R$ is involved. The present invention is also directed to a composition for regulating function of a cell by binding to $IP_3R$ and regulating the function of $IP_3R$, and to a regulation method using the same.

BRIEF DESCRIPTION OF THE DRAWINGS

FIG. 5 shows structures of mutants in which different lengths of parts on N-terminal and C-terminal sides in CARP and $IP_3R1$ are deleted, and interactions between CARP mutants and MD2, CARP and $IP_3R1$ mutants, analyzed by β-gal assay based on the yeast two-hybrid system (n=3). β-gal assay is evaluated by the time of blue colony appearance, i.e., blue colony appears within 30 min (+++), 2 h (++) and 8 hr (+).

BEST MODE FOR CARRYING OUT THE INVENTION

Inositol-1,4,5-triphosphate ($IP_3$) receptor ($IP_3R$) is a $Ca^{2+}$ releasing path that is induced by intracellular $IP_3$, and $IP_3R$ finely controls intracellular release of $Ca^{2+}$ by binding with a variety of substances. The inventors of the present application analyzed the substances that bind to $IP_3R$ and control release of calcium by $IP_3$, and identified a novel protein capable of binding to $IP_3R$. The inventors also found that this protein is a protein known as a carbonic anhydrase-related protein (CARP).

The inventors of the present application demonstrated that CARP is expressed in only a Purkinje cell of cerebellum that abundantly expresses $IP_3R$, and examined and analyzed the effect of CARP on $IP_3R$.

Accordingly, the purpose of the present invention is to control a mechanism of intracellular release of calcium, as well as to control signal transmission in which intracellular calcium is involved. Another purpose of the present invention is to control intracellular calcium release by carbonic anhydrase-related protein (CARP), to regulate or diagnose the activity of $IP_3R$.

The present invention relates to a regulator for the activity of inositol-1,4,5-triphosphate($IP_3$) receptor ($IP_3R$) comprising carbonic anhydrase-related protein (CARP).

Also the present invention relates to a control agent for intracellular calcium release comprising a carbonic anhydrase-related protein (CARP), and a method of control therewith.

$IP_3R$ is related with a variety of regulating factors such as $Ca^{2+}$, $Ca^{2+}$-calmodulin, FK506 binding protein 12K, ATP and kinase. Many of these factors are considered to regulate the function of $IP_3R$ by binding to the center part of $IP_3R$ or by phosphorylation.

In order to screen for novel regulators of $IP_3R$, the inventors of the present application screened a mouse cerebral cDNA library by the yeast two-hybrid system using a modulatory domain of $IP_3R1$ as a bait.

Figure 1:
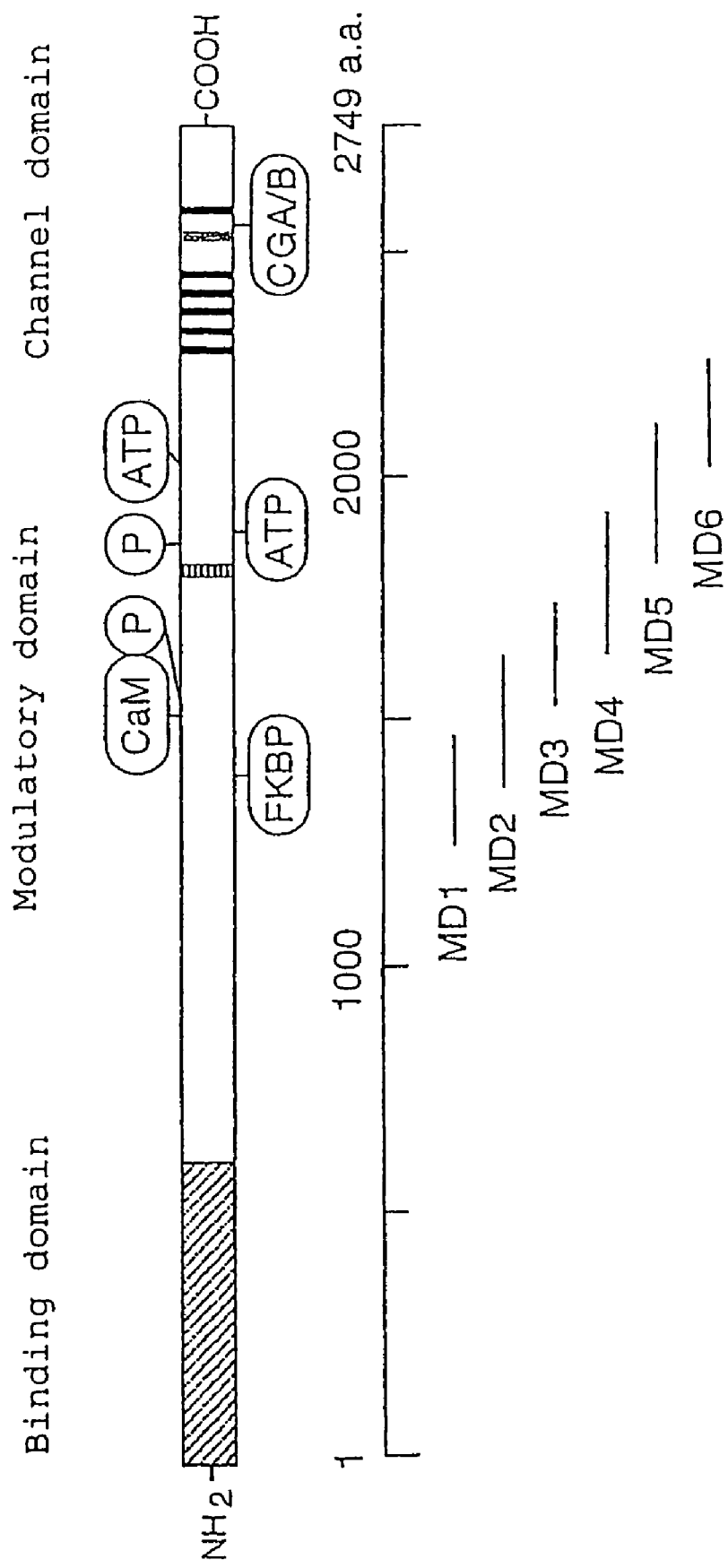
FIG. 1 schematically shows locations of substances binding to three domains and modulatory domain and the like of $IP_3P1$, together with six bait constructs used in the present invention.

FIG. 1 schematically shows a ligand binding domain, a modulatory domain and a channel domain of mouse $IP_3R$ Type 1 ($mIP_3R1$) The number shown in the middle stage of FIG. 1 is the number of amino acid. In the modulatory domain of FIG. 1, FK506 binding protein (FKBP) (amino acid number:1400-1401), Ca$^{2+}$-calmodulin (CaM) (amino acid number:1564-1585), putative ATP binding sites (ATP) (amino acid number:1773-1778, 1775-1780 and 2016-2021), and for serine residue (amino acid: 1588, 1755) for phosphorylation are shown. A binding site for chromogranin A and B (CGA/B) is shown in the channel domain (between the fifth and the sixth transmembrane sites). The inventors of the present application used a part of this modulatory domain as a bait. FIG. 1 also shows positions MD1 to MD6 that correspond to the six baits used in the present invention.

The amino acids 1245-2264 of mIP$_3$R1 was separated into overlapping six constructs and cDNA constructs corresponding to these constructs were used as baits. Amino acid residues 1245-2264 of the IP$_3$R1 modulatory domain was mapped and 6 bait constructs (MD1 to MD6) were prepared by PCR method using the respective primer sets overlapping with the map and shown below, each comprising a sense strand (S) and an antisense strand (A).

```
MD1 (mIP3R1: 1245-1464 amino acids):
                                       (SEQ ID NO: 3)
(S): 5'-GGGAATTCGGTGGAGGTTGTGCAGGCAACCAGCAGAATC-3'

(SEQ ID NO: 4)
(A): 5'-GGGGGTCGACGTGTTGTTACAGGCCCTGCAGA-3'

MD2 (mIP3R1: 1387-1647 amino acids)
                                       (SEQ ID NO: 5)
(S): 5'-GGGAATTCGGTGGAGGCAAGAATGTGTACACGGAGA-3'

(SEQ ID NO: 6)
(A): 5'-GGGGGTCGACCTCACATTTCCTCCTGGCATC-3'

MD3 (mIP3R1: 1593-1785 amino acids)
                                       (SEQ ID NO: 7)
S): 5'-GGGAATTCGGAGGAGGATCCAGAGACTACCGAAATATCAT-3'

(SEQ ID NO: 8)
(A): 5'-GGGGGTCGACGCTTGTGGAACTAGATCCAGGACC-3'

MD4 (mIP3R1: 1685-1943 amino acids)
                                       (SEQ ID NO: 9)
(S): 5'-GGGAATTCGGTGGAGGAGACAGAGGCTATGGAGAGAAG-3'

(SEQ ID NO: 10)
(A): 5'-GGGGGTCGACTCCCCAGACTGGTAATGGTCA-3'

MD5 (mIP3R1: 1865-2160 amino acids)
                                       (SEQ ID NO: 11)
(S): 5'-GGGAATTCGGTGGAGGAGTGGCCCAGCAGGAAATCAA-3'

(SEQ ID NO: 12)
(A): 5'-GGGGGTCGACGGTGAGCGAGGATGTAGATG-3'

MD6 (mIP3R1: 2015-2264 amino acids)
                                       (SEQ ID NO: 13)
(S): 5'-GGGGGTCGACCCGGAGGAGGCCTTGGTCTTCTTGG-3'

(SEQ ID NO: 14)
(A): 5'-GGGGGTCGACAGACAGGCTGGGCTCGAAGT-3'
```

Each cDNA obtained by the PCR was digested with either EcoRI and SalI or SalI alone, then ligated to pGBT9 (Clontech Laboratories Inc.). All of the plasmid constructs were sequenced to confirm that the cloning of appropriate cDNAs was translationally in-frame and devoid of PCR-induced errors.

Amino acid sequence of amino acids 1387 to 1647 of mIP$_3$R1 corresponding to MD2 is shown by SEQ ID NO: 1 in the sequence listings.

The primary screening with bait constructs MD1, 3, 4, 5 and 6 yielded several tens of candidate substances that were unlikely to be IP$_3$R1 binding protein, due to translational frame-shifting or the presence of regions known to be untranslated sequence. The inventors, however, obtained 13 positive clones in the screening with MD2 construct. DNA sequencing analysis revealed that all encodes a carbonic anhydrase-related protein (CARP). These clones contain different lengths of 5' UTR of CARP cDNA followed by a full-length coding region in frame.

An amino acid sequence consisting of 291 amino acids of mouse carbonic anhydrase-related protein (CARP) is shown in SEQ ID NO:2 of the sequence listings The constructs MD1 and MD2 contained a putative FKBP12 binding site, however, FKBP was not found from positive clones in the yeast two-hybrid screening. Our observation could support the recent report that FKBP12 does not bind to IP.sub.3R1 (see prior art document 10, Bultynck G, De Smet P. et al., (2001), Biochem J., 354, 413-22). Alternatively, it is probably due to amplitude of the cDNA library or requirements of additional protein(s) for FKBP-binding to IP$_3$R1. However, in any case, FKBP was not found in this experiment. MD2 constructs have a calmodulin binding site. The inventors, however, did not detect carmodulin-binding in this screening, because calmodulin-binding to IP$_3$R1 is Ca$^{2+}$-dependent.

Carbonic anhydrase-related protein (CARP) has been known to be highly expressed in Purkinje cells of cerebellum, but tissue distribution has not been extensively studied so far. The inventors first examined tissue distribution of CARP by Western blot analysis.

Figure 2:
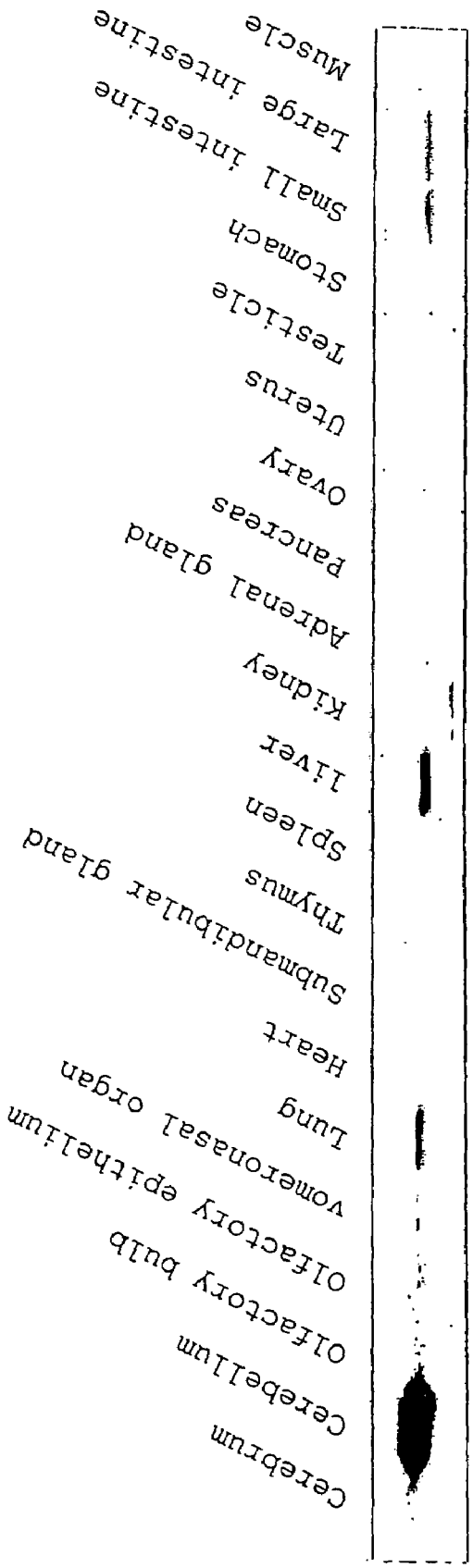
FIG. 2 is a photograph substituted for drawing showing a result of Western blotting conducted for evaluation of tissue distribution of carbonic anhydrase-related protein (CARP). The soluble fraction (10 μg/lane) was subjected to 5% polyacrylamide gel electrophoresis in the presence of sodium dodecyl sulfate, transferred to nitrocellulose and detected with 2 μg/ml of anti-CARP polyclonal antibody.

The result is shown in a photograph of FIG. 2 which is substituted for drawing. FIG. 2 shows expression of CARP in soluble fraction from various organs. CARP protein was predominantly expressed in cerebellum as reported previously, where IP$_3$R1 is also expressed abundantly. Low level expression was observed in cerebrum, olfactory bulb, olfactory epithelium, vomeronasal organ, lung, submandibular gland, liver, adrenal gland, stomach, small intestine and large intestine. No signal was observed in heart, thymus, spleen, pancreas, ovary, uterus, testicle and muscle.

Figure 3:
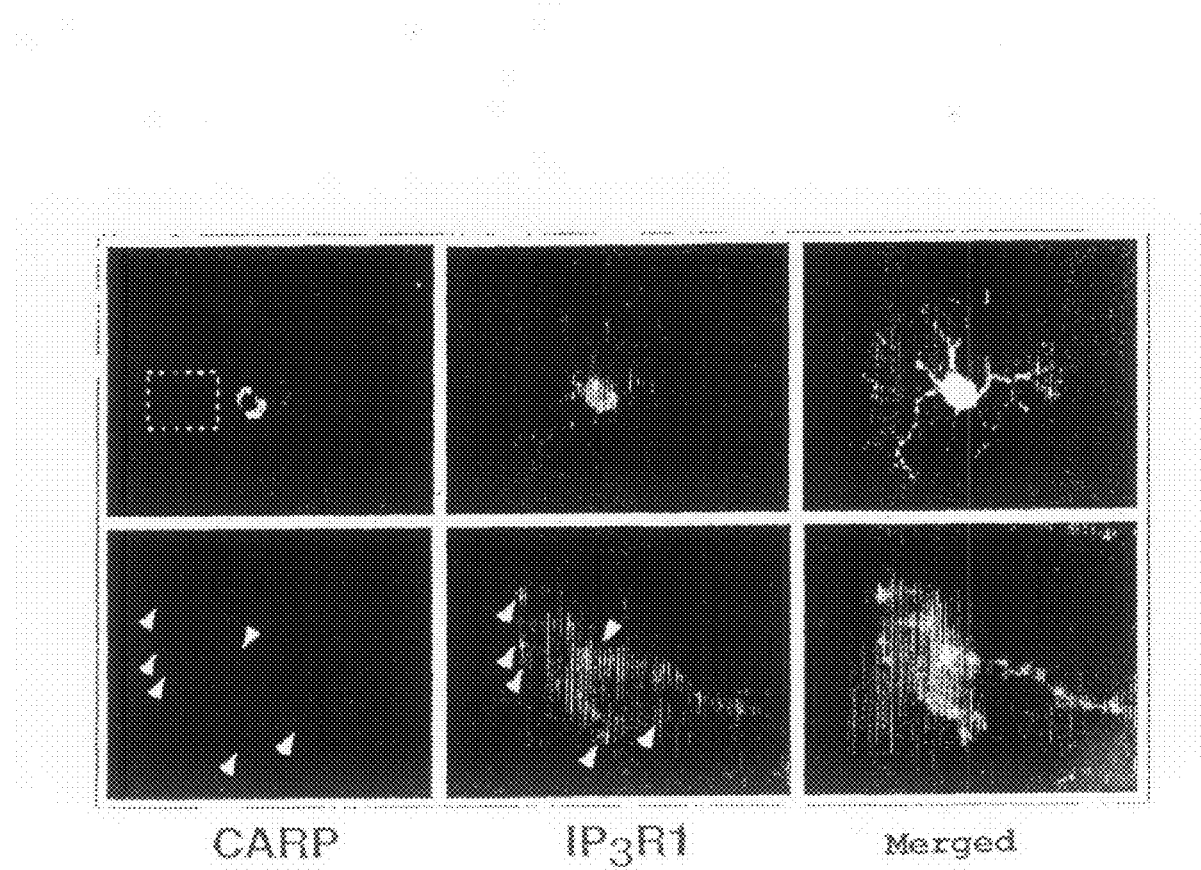
FIG. 3 are photographs substituted for drawings respectively showing a cultured Purkinje cell immunostained with anti-CARP antibody (left view in FIG. 3), a cultured Purkinje cell immunostained with anti $IP_3R1$ antibody (middle view in FIG. 3) and a view obtainable by merging these (right view in FIG. 3). The arrows represent exemplary locations of CARP and $IP_3R1$.

Immunohistochemical analysis of cerebellum revealed that CARP is expressed predominantly in cytoplasm of cerebellar Purkinje cells as well as IP$_3$R1. IP$_3$R1 in Purkinje cells is abundantly expressed and widespread, but not homogeneous especially in dendrites due to formation of cluster. If CARP binds to IP$_3$R1, CARP protein distribution would not be homogeneous and could co-localize with IP$_3$R1, although CARP is a cytosolic soluble protein. To define intracellular localization of CARP and IP$_3$R1 in Purkinje cells, the inventors prepared primary cultured Purkinje cells for immunohistochemical analysis. FIG. 3 provides photographs substituted for drawings, showing expression of CARP and IP$_3$R1 in Purkinje cells visualized by a double staining technique. The left photos in FIG. 3 are those immunostained with anti-CARP antibody, the middle pictures are those immunostained with anti-IP$_3$R1 antibody, and the right pictures are those obtained by merging the left two photos. The upper photos in FIG. 3 are whole images of the cultured Purkinje cells and the lower pictures are enlarged views thereof. The arrows indicate examples of localization of CARP and IP$_3$R1.

As can be seen from FIG. 3, both of them are expressed in cytoplasm, dendrites and axon. Intracellular localization clarified that CARP and IP$_3$R1 form cluster to co-localize (see arrows in FIG. 3). Abundant and highly specialized co-expression of CARP and IP$_3$R1 and co-localization in Purkinje cells could suggest physiological coupling of these proteins through binding.

Figure 4:
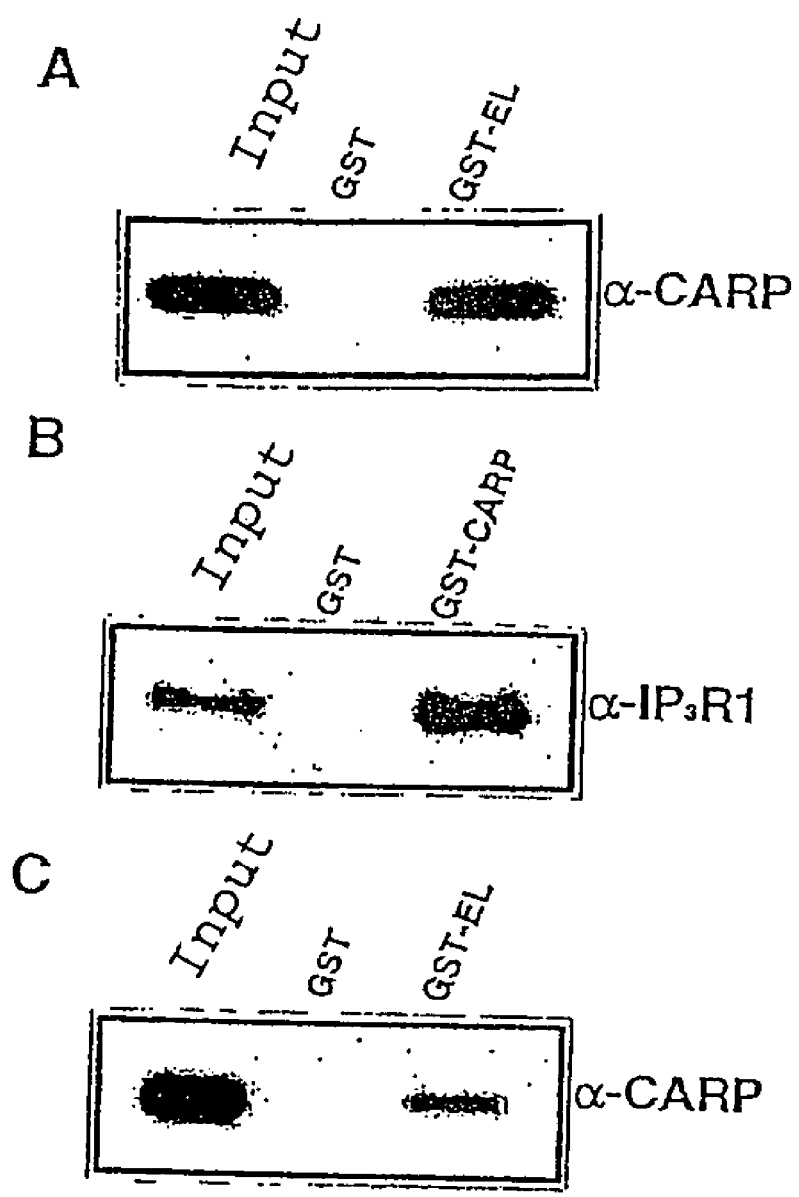
FIG. 4A is a photograph substituted for drawing showing a result of Western blotting analysis with anti-CARP antibody for a glutathione eluate from a pull-down assay through glutathione-Sepharose conducted for proteins bound as a result of incubation of cytosolic fraction of mouse cerebellum in the presence of GST-EL or GST.
FIG. 4B is a photograph substituted for drawing showing a result of immunoblot analysis with anti-$IP_3R1$ antibody KM1112 conducted for proteins that are bound in a pull-down assay using GST-CARP or GST carried out in the manner as described in FIG. 4A for a detergent extract of mouse cerebellum microsome.
FIG. 4C is a photograph substituted for drawing showing a result of immunoblot analysis with anti-CARP antibody conducted for proteins that are bound in a pull-down assay using GST-CARP or GST for purified CARP-His.

Next, the inventors of the present application examined the interaction between CARP and IP$_3$R1 by means of a pull-down method in order to obtain further evidence for the interaction by biochemical methods. The inventors first developed expression system in Sf9 cells, and made IP$_3$R1 soluble by removing the channel domain. The soluble IP$_3$R1, designated GST-EL, covers both the ligand binding domain and modulatory domain (amino acids 1-2217 of mIP$_3$R1) and has GST in its N terminus. Mouse cerebellar cytosolic fraction was incubated with GST-EL or GST, and binding of CARP to the recombinant proteins was analyzed by immunoblotting with anti-CARP antibody. The results are shown in photographs of FIG. 4 which are substituted for drawings. FIG. 4A shows a result of Western blotting analysis with anti-CARP antibody for a glutathione eluate from a pull-down assay through glutathione-Sepharose conducted for proteins bound as a result of incubation of cytosolic fraction of mouse cerebellum in the presence of GST-EL or GST. FIG. 4B shows a result of immunoblotting analysis with anti-IP$_3$R1 antibody KM1112 conducted for proteins that are bound in a pull-down assay using GST-CARP or GST carried out in the manner as described in FIG. 4A for a detergent extract of mouse cerebellum microsome. FIG. 4C shows a result of immunoblotting analysis with anti-CARP antibody conducted for proteins that are bound in a pull-down assay using GST-EL or GST for purified CARP-His.

These results demonstrated that CARP specifically binds to GST-EL, but not to GST alone. In the reciprocal experiment, the detergent extract of mouse cerebellar microsome was processed for pull-down assay with GST-CARP, and binding of IP$_3$R1 was analyzed with anti-IP$_3$R1 antibody. As shown in FIG. 4B, IP$_3$R1 interacted with GST-CARP but not with GST. To determine whether the binding of CARP to IP$_3$R1 is made directly, pull-down assay was conducted for purified CARP with His tag using GST-EL. As shown in FIG. 4C, CARP-His bound specifically to GST-EL, indicating that the interaction between CARP and IP$_3$R1 is direct.

Considering all the results above, these findings show that CARP is a novel IP$_3$R1 binding protein.

To determine the respective interaction domains of CARP and IP$_3$R1, truncated mutants of both genes were prepared and analyzed using yeast two-hybrid system. FIG. 5 shows structures of mutants in which different lengths of parts on N-terminal and C-terminal sides in CARP (upper chart in FIG. 5) and IP$_3$R1 (lower chart in FIG. 5) are deleted. Interactions between CARP mutants and MD2, CARP and IP$_3$R1 mutants were analyzed by β-gal assay by the yeast two-hybrid system. The prepared mutant and results of β-gal assay in the yeast two-hybrid system (n=3) are shown in FIG. 5. β-gal assay was evaluated by the time of blue colony appearance, i.e., blue colony appears within 30 min (+++), 2 h (++) and 8 hr (+).

Weak binding activity was found in case of deletion of N-terminal 44 amino acids of CARP and the binding activity to IP$_3$R1 was lost in case of deletions of the other parts. This indicates that minimum binding site of CARP to IP$_3$R1 is 45-291 amino acids. In case of IP$_3$R1, the inventors found that 1387-1647 amino acids are necessary for binding with CARP.

Next, an effect of CARP on binding of IP$_3$ was studied.

IP$_3$-induced Ca$^{2+}$ release in intact Purkinje cells are known to require much higher concentration of IP$_3$ (EC$_{50}$≧10 μM) by comparison to other tissues or isolated IP$_3$R1 (EC$_{50}$=100 nM to 1 μM). According to the experimental results by the present inventors as described above, it was demonstrated that CARP was predominantly expressed in Purkinje cells together with IP$_3$R1 and bound to IP$_3$R1. It has been also known that sensitivity of IP$_3$R1 to IP$_3$ is significantly reduced in a Purkinje cell, and the inventors speculated that the lower sensitivity might be due to expression of CARP in Purkinje cells. Accordingly, the inventors of the present application analyzed the inhibiting effects of CARP on IP$_3$ binding.

The inventors conducted a binding assay using purified IP$_3$R1, to evaluate effect of CARP on IP$_3$-binding affinity to IP$_3$R1. Purified IP$_3$R1 was incubated with various concentration of [$^3$H] IP$_3$ in the presence or absence of purified recombinant CARP, and analyzed by a Scatchard plot.

Figure 6:
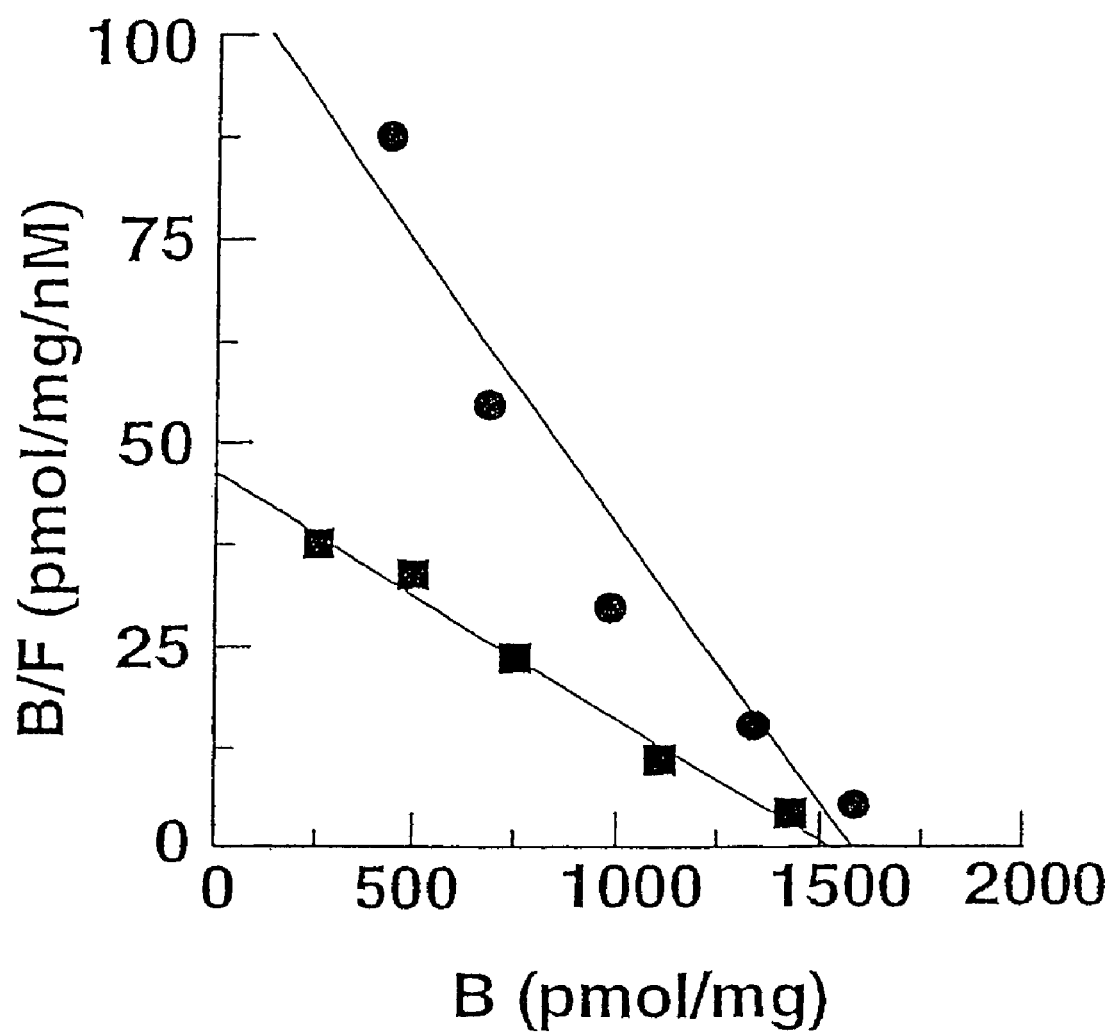
FIG. 6 shows an inhibiting effect of CARP on binding of $IP_3$ to $IP_3R1$, indicated by a Scatchard plot. The closed square (■) shows the case where CARP is present, and the closed circle (●) shows the case where CARP is absent. The mean (Kd±S.D.) from three separate experiments conducted in the presence or in the absence of CARP were, 33.5±2.07 nM and 18.2±4.58 nM, respectively.

FIG. 6 shows a result of Scatchard plot analysis regarding inhibition of specific [$^3$H] IP$_3$ binding to IP$_3$R1 by IP$_3$ in the presence (■ in FIG. 6) and in the absence (● in FIG. 6) of CARP. In FIG. 6, the horizontal axis represents an amount of binding IP$_3$ (pmol/mg), and the vertical axis represents an amount of binding IP$_3$ divided by an amount of non-binding IP$_3$ (pmol/mg/nM).

The result shows that mean value of dissociation constant (Kd±S.D.) of IP$_3$ binding to IP$_3$R1 in the presence or absence of CARP was33.5±2.07 nM and 18.2±4.58 nM, respectively. Bmax value in the presence or absence of CARP was 1630±108 pmol/mg and 1720±234 pmol/mg, respectively, which proved that the maximum number of IP$_3$-binding sites were unaltered by CARP. These results also show that CARP inhibits binding of IP$_3$ to IP$_3$R1 not by antagonistic action but by reducing the affinity. The inventors speculate that CARP changes the conformation of IP$_3$R1 by binding and reduces sensitivity to IP$_3$.

A high density of IP$_3$R1 has been proposed to be one of the factors contributing to low IP$_3$-sensitivity in IP$_3$-induced Ca$^{2+}$ release in Purkinje cells (Ogden, D. and Capiod, T. (1997), J. Gen. Physiol., 109, 741-56). In addition to this explanation, the inventors now provide an additional explanation for this, that inhibitory effects of CARP on IP$_3$-binding to IP$_3$R1 results in low sensitivity to IP$_3$ in a Purkinje cells.

In the foregoing description, inositol-1,4,5-triphosphate (IP$_3$) receptor (IP$_3$R) of the present invention was derived from mouse, however, IP$_3$R of the present invention may be derived from animals such as nematomorph and *drosophila*, preferably mammalian such as human, mouse, rat, hamster, monkey, dog, rabbit and the like without limited to mouse. In the foregoing description, subtype 1 of IP$_3$R was used, however, other subtypes may be examined for binding property in a similar manner as described above. Therefore, the present invention embraces all of the subtypes of IP$_3$R in the absence of any special condition. Preferred subtypes include subtype 1 as described above.

The carbonic anhydrase-related protein (CARP) of the present invention may be naturally occurring or produced by recombinant technique based on genetic information. CARP of the present invention may be derived from animals such as nematomorph and *drosophila*, preferably mammalian such as human, mouse, rat, hamster, monkey, dog, rabbit and the like without limited to the mouse as described above. CARP used in the present invention is preferably, but not limitedly, derived from the same kind of animal from which IP$_3$R in use is derived. CARP of the present invention may be of whole length, but it may have a minimum amino acid sequence required for binding with IP$_3$R, for example, at least amino acids 45-291 in the case of mouse. Preferred examples of CARP include those having naturally-occurring amino acid sequence, however, CARP may have a naturally-occurring amino acid sequence from which one or more of the amino acid is deleted, added, and/or substituted with other amino acid insofar as the binding ability with IP$_3$R is maintained.

The present invention provides a regulator for the activity of IP$_3$R comprising carbonic anhydrase-related protein (CARP), and the regulator for the activity according to the present invention may be comprised of CARP alone but may be a composition including a biologically acceptable carrier such as buffer. The regulator for the activity according to the present invention e should change, increase or suppress the activity of $IP_3R$ on $IP_3$, compared to the case where CARP is absent. In the above-described example using mouse, suppression of activity is exemplified. Concentration of CARP in use may be any concentration that is able to change the activity of $IP_3R$.

The present invention also provides a control agent for intracellular calcium release comprising carbonic anhydrase-related protein (CARP), and the control agent of the present invention may be comprised of CARP alone but may be a composition such as pharmaceutical composition comprising a biologically or pharmaceutically acceptable carrier such as buffer. The control agent of the present invention should be able to control, decrease or increase the amount of intracellular calcium release in the presence of CARP. Concentration of CARP in use is not particularly limited, and may be any concentration at which amount of intracellular calcium release is controllable without causing any side effect or toxicity. Control of intracellular calcium release in the present invention is preferably, but not limitedly, control of release of calcium that is induced by inositol-1,4,5-triphosphate ($IP_3$).

The present invention also provides a method of controlling intracellular calcium release that comprises adding carbonic anhydrase-related protein (CARP) to the cell. The cell intended in this method of the present invention is a cell constituting a biological body, preferably a cell having $IP_3R$. This method of the present invention is widely applicable to therapy and diagnosis, as well as for analyzing the action of $IP_3$ as an intracellular second messenger or for assaying the intracellular activity of $IP_3R$.

The present invention demonstrates that carbonic anhydrase-related protein (CARP) is a substance that specifically binds to $IP_3R$, preferably $IP_3R1$, and detection and identification of $IP_3R$ by CARP are also embraced in the present invention. For such object, labeling of CARP in a suitable manner, as well as detection, identification and quantification of $IP_3R$ by using the CARP thus labeled are also possible.

Complete contents described in the specification of Japanese Patent Application No. 2003-141083 are incorporated herein.

EXAMPLES

The present invention will be now explained more specifically by way of examples, however, the present invention is not limited by these examples in any way.

Yeast two-hybrid assay in the following examples was conducted using MATCHJMAKER™ Two-Hybrid system according to the manufacturer's protocol (Clontech Laboratories Inc., Palo Alto, Calif., USA).

Example 1

Design and Synthesis of the Bait Constructs

Using a part of the $IP_3R1$ modulatory domain shown in FIG. 1 as bait, six kinds of baits were designed.

Amino acids 1245-2264 of mouse $IP_3R1$ ($mIP_3R1$) was divided into overlapping 6 constructs, and respective cDNA constructs corresponding to these 6 c constructs were used as baits. Amino acid resides 1245-2264 of the $IP_3R1$ modulatory domain was mapped, and using primer sets as listed below each including a sense strand (S) and an antisense strand (A), six bait constructs (MD1 to MD6) were prepared by PCR.

MD1 ($mIP_3R1$: 1245-1464 amino acids):
(SEQ ID NO: 3)
(S): 5'-GGGAATTCGGTGGAGGTTGTGCAGGCAACCAGCAGAATC-3'

(SEQ ID NO: 4)
(A): 5'-GGGGGTCGACGTGTTGTTACAGGCCCTGCAGA-3'

MD2 ($mIP_3R1$: 1387-1647 amino acids)
(SEQ ID NO: 5)
(S): 5'-GGGAATTCGGTGGAGGCAAGAATGTGTACACGGAGA-3'

(SEQ ID NO: 6)
(A): 5'-GGGGGTCGACCTCACATTTCCTCCTGGCATC-3'

MD3 ($mIP_3R1$: 1593-1785 amino acids)
(SEQ ID NO: 7)
(S):
5'-GGGAATTCGGAGGAGGATCCAGAGACTACCGAAATATCAT-3'

(SEQ ID NO: 8)
(A): 5'-GGGGGTCGACGCTTGTGGAACTAGATCCAGGACC-3'

MD4 ($mIP_3R1$: 1685-1943 amino acids)
(SEQ ID NO: 9)
(S): 5'-GGGAATTCGGTGGAGGAGACAGAGGCTATGGAGAGAAG-3'

(SEQ ID NO: 10)
(A): 5'-GGGGGTCGACTCCCCAGACTGGTAATGGTCA-3'

MD5 ($mIP_3R1$: 1865-2160 amino acids)
(SEQ ID NO: 11)
(S): 5'-GGGAATTCGGTGGAGGAGTGGCCCAGCAGGAAATCAA-3'

(SEQ ID NO: 12)
(A): 5'-GGGGGTCGACGGTGAGCGAGGATGTAGATG-3'

MD6 ($mIP_3R1$: 2015-2264 amino acids)
(SEQ ID NO: 13)
(S): 5'-GGGGGTCGACCCGGAGGAGGCCTTGGTCTTCTTGG-3'

(SEQ ID NO: 14)
(A): 5'-GGGGGTCGACAGACAGGCTGGGCTCGAAGT-3'

Resulting cDNAs obtained by the PCR were digested with EcoRI and SalI, or with SalI alone, then ligated to pGBT9 (Clontech Laboratories Inc.). All of the resultant plasmids were sequenced to confirm that cloning of the appropriate cDNAs was translationally in-frame and devoid of PCR-induced errors.

Example 2

Construction of cDNA Library

Mouse brain cDNA library was constructed in pGAD-GL (Clontech Laboratories Inc.). In brief, total RNA from mouse brains (6-week old ddY mouse; Nippon SLC, Hamamatsu, JAPAN) was enriched for poly(A)$^+$mRNA expression by using oligo (dT)-cellulose chromatography. Double-stranded cDNAs were generated using random hexamers as primers, and were ligated to EcoRI adapters. After digestion with EcoRI, cDNAs over 400 bp were collected by the size fractionation using Sepharose CL2B (Amersham Biosciences Inc., Piscataway, N.J., USA), and inserted into EcoRI site of pGAD GL. Approximately $5 \times 10^5$ independent clones were generated in *Escherichia coli* XL1-Blue MRF (Stratagene, La Jolla, Calif., USA), and plasmid DNA was isolated after one amplification.

Example 3

Preparation of Antibodies

Monoclonal antibodies against mIP$_3$R1, 4C11, 18A10 and KM1112 were prepared according to the method (Maeda, N., Niinobe, M., et al., (1988), J. Neurochem., 51, 1724-1730; Maeda, N., Niinobe, M., et al, (1990), EMBO J., 9, 61-67: Sugiyama, T., Furuya, A., et al., (1994), FEBS Letters, 354, 149-154). A peptide corresponding to amino acid residues 267-279 (CDGILGDNFRPTQ; residues 267-279 of SEQ ID NO:2) of mouse CARP which is diverse in carbonic anhydrase family was synthesized, and this peptide was conjugated to keyhole limpet hemocyanin (KLH) via N-terminal Cys residue, using m-maleimidobenzoyl N-hydroxysuccinimide ester (MBS). A polyclonal antibody was raised in rabbits (New England White, Hokudo Tohya Immunity Laboratory, Hokkaido, Japan). The antibody was purified from antisera using antigenic peptide-conjugated beads according to a standard protocol.

Example 4

Western Blot Analysis of CARP Expression

Expression of CARP in various organs was analyzed by Western blotting. Each organ dissected from mice were homogenized in homogenizing buffer (0.32M sucrose, 1 mM EDTA, 1 mM 2-mercaptoethanol, protease inhibitors (0.1 mM phenylmethylsulfonyl fluoride, 10 µM leupeptin, 10 µM pepstatin A, 10 µM E-64) and 10 mM Tris-HCl pH7.4), using a glass-Teflon™ homogenizer. For preparations from heart, liver, kidney, adrenal gland, testis and muscle, these organs were minced with scissors into small pieces before homogenize. The homogenate was centrifuged at 100,000×g at 4° C. for 20 minutes. The resultant supernatant (10 µg) was used for 5% polyacrylamide gel electrophoresis in the presence of sodium dodecyl sulfate, transferred to nitro cellulose, and immuno-detected with anti-CARP antibody. The results are shown in FIG. 2.

Example 5

Immunohistochemistry

Preparation and immunohistochemical analyses of primary cultured Purkinje cells of cerebellum were conducted according to the method (Yuzaki, M., and Mikoshiba, K., (1992), J. Neurosci., 12, 4253-63.). Following combination of primary and secondary antibodies were used for double staining, rabbit anti-CARP polyclonal antibody and FITC-conjugated anti-rabbit IgGantibody, anti-IP$_3$R1 monoclonal antibody, 18A10 and TexasRed-conjugated anti-rat IgG antibody. The results are shown in FIG. 3.

Example 6

Expression of a Recombinant IP$_3$R1 Channel Domain Deletion in Sf9 Cells

The DNA encoding the N-terminal region of mouse IP$_3$R1 (residues 1 to 225) was inserted into glutathione S-transferase (GST) fusion vector pGEX-KG. The GST-IP$_3$R1 (1-225) fragment was subcloned into the baculovirus transfer vector pBlueBac4.5 (Invitrogen). The 3'-region downstream from the Sma I site of GST-IP$_3$R1 (1-225) was replaced with the Sma I-EcoRI fragment of mouse IP$_3$R1 (corresponding to residues 79-2217) to generate GST-IP$_3$R1 (1-2217) (termed GST-EL) construct. Recombinant baculovirus carrying GST-EL was generated using Bac-N-Blue™ Transfection Kit (Invitrogen) according to the manufacturer's protocols. GST-EL was expressed in 2×10$^8$ Sf9 cells by infecting recombinant baculoviruses at a multiplicity of infection of 5, and incubating for 48 hours. Cells expressing GST-EL were homogenized in 10 mM HEPES (pH7.4), 100 mM NaCl, 2 mM EDTA, 1 mM 2-mercaptoethanol, 0.1% Triton X-100, and protease inhibitors, using a glass-Teflon™ homogenizer. The homogenate was centrifuged at 20,000×g for 30 minutes. GST-EL was purified from the supernatant using glutathione-Sepharose 4B (Amersham Pharmacia Biotech Inc.) in accordance with the recommendation of the vender,

Example 7

Expression of Recombinant CARP in *Escherichia coli*

Full-length CARP cDNA was cloned into Nde I and Hind III sites of pET23a vector (Stratagene) in frame for transcription, thereby introducing His-tag into C-terminus of recombinant CARP. A single colony of *Escherichia coli* BL21 (DE3) transformed with CARP expression vector was incubated in 1.5 ml of Luria-Bertani medium containing 100 µg/ml ampicillin at 37° C. for 10 hr. One milliliter of the culture was inoculated into 1L of Luria-Bertani medium containing 100 µg/ml ampicillin and incubated at 25° C. until it reached an A$_{600}$ of 0.7, and then the culture was supplemented with isopropylthio-β-D-galactoside (final concentration, 0.5 mM). Incubation was continued at 25° C. for 8 h and cells were harvested by centrifugation, washed with 10 ml of phosphate-buffered saline (PBS) and sonicated in 50 ml of PBS at 4° C. After centrifugation to remove insoluble material, the supernatant was applied to a High-Trap Chelating column (Amersham Biosciences). The recombinant CARP protein was purified first according to the manufacturer's protocol, then by Mono Q anion exchange chromatography (Amersham Biosciences), and finally dialyzed against the buffer used in the pull-down experiment or the IP$_3$-binding experiment to exchange buffer.

For GST-fusion recombinant CARP, full-length CARP cDNA was cloned into Bam HI and Xho I sites of pGEX-KG to generate GST-CARP construct. GST-CARP was expressed in *Escherichia coli* and purified using glutathione-Sepharose as mentioned above.

Example 8

Biochemical Analysis of CARP-Binding to IP$_3$R1

Adult mouse cerebella were homogenized in 10 mM HEPES (pH 7.4), 320 mM Sucrose, 2 mM EDTA, 1 mM 2-mercaptoethanol, and protease inhibitors and the homogenate was centrifuged at 1,000×g for 10 min. The supernatant was centrifuged at 100,000×g for 60 min to obtain the cytosolic fraction (the supernatant) and the crude microsome (the pellet). The cytosolic fraction was added with 100 mM NaCl, and incubated with 20 µg of GST-EL or GST for 2 hours at 4° C. After adding 10 µL of glutathione-Sepharose and another 2-hours incubation, the resins were washed five times with wash buffer (10 mM HEPES (pH 7.4), 100 mM NaCl, 2 mM EDTA, 1 mM 2-mercaptoethanol, and 0.01% Triton X-100), and bound proteins were eluted with 20 mM glutathione. The eluted proteins were analyzed by Western blotting with anti-CARP antibody.

The crude microsome was solubilized with 1% Triton X-100, and dissolved in 50 mM HEPES (pH7.4), 2 mM EDTA, 1 mM 2-mercaptoethanol, and protease inhibitors for 30 min at 4° C., and centrifuged at 20,000×g for 30 min. The supernatants were processed for pull-down assay with 10 µg of GST-CARP or GST as described above, and bound proteins were subjected to immunoblot analysis with anti-$IP_3R1$ antibody KM1112.

For direct binding assay, pull-down assay was conducted for CARP-His (5 µg) purified in wash buffer, using GST-EL or 20 µg of GST as described above, and bound proteins were subjected to immunoblot analysis with anti-CARP antibody. Experiments were repeated at least three times to confirm results. The results are shown in FIG. 4.

Example 9

Identification of Binding Sites by Yeast Two-hybrid Assay

In order to determine the binding site, either of $IP_3R1$ or CARP constructs was truncated by using each of pGBT9 and pGAD-GL.

$IP_3R1$ truncated constructs contain the following amino acids:
pGBT9-ΔI1 (m$IP_3R1$: 1387-1464 amino acids);
pGBT9-ΔI2 (m$IP_3R1$: 1387-1520 amino acids);
pGBT9-ΔI3 (m$IP_3R1$: 1387-1598 amino acids);
pGBT9-ΔI4 (m$IP_3R1$: 1513-1598 amino acids);
pGBT9-ΔI5 (m$IP_3R1$: 1513-1647 amino acids).

CARP truncated constructs contain the following amino acids:
pGAD-GL-ΔC1 (CARP; 1-127 amino acids);
pGAD-GL-ΔC2 (CARP; 1-147 amino acids);
pGAD-GL-ΔC3 (CARP; 1-170 amino acids);
pGAD-GL-ΔC4 (CARP; 1-180 amino acids);
pGAD-GL-ΔC5 (CARP; 1-217 amino acids);
pGAD-GL-ΔC6 (CARP; 1-234 amino acids);
pGAD-GL-ΔC7 (CARP; 45-291 amino acids);
pGAD-GL-ΔC8 (CARP; 121-291 amino acids); and
pGAD-GL-ΔC9 (CARP; 184-291 amino acids).

All of these plasmid constructs were sequenced to confirm that cloning of the appropriate cDNAs was in-frame for transcription.

The results are shown in FIG. 5.

Example 10

[$^3$H]$IP_3$ Binding Assay

[$^3$H]$IP_3$ binding to $IP_3R1$ was assayed by polyethylene glycol precipitation in the presence or absence of CARP in accordance with the method as reported previously (Maeda, N., Niinobe, M., et al, (1990), EMBO J.,9,61-67). 0.5 µg of purified $IP_3R1$ was incubated with or without 10 µg of purified His-CARP in 50 µL of a solution containing 50 mM Tris-HCl, pH 8.0, 1 mM EDTA, 1 mM 2-mercaptoethanol, 9.6 nM [$^3$H] $IP_3$ and different concentration of $IP_3$, for 10 min at 4° C. Nonspecific binding was measured in the presence of 10 µM $IP_3$. The results are shown in FIG. 6.

INDUSTRIAL APPLICABILITY

The present invention provides a novel substance capable of binding to $IP_3R$, and provides means for controlling intracellular calcium release caused by the activity of $IP_3R$. The regulator of the present invention is able to control intracellular calcium release inducted by $IP_3$, and hence is useful in therapy and diagnosis of a variety of diseases caused by abnormal release of calcium. It also provides effective means for analyzing the action of $IP_3$ as an intracellular second messenger.

Also, the present invention clarified a novel function of CARP that had not been elucidated, and provides new application of control of calcium release in CARP cells.

The invention claimed is:

1. A method of reducing intracellular calcium release in a cell comprising adding carbonic anhydrase-related protein (CARP) to the cell wherein the carbonic anhydrase-related protein consists of an amino acid sequence of amino acids 45 to 291 of SEQ ID NO: 2, thereby the intracellular release of calcium is reduced.

2. The method of claim 1 wherein the carbonic anhydrase-related protein is added into the cell as a protein.

3. The method of claim 1, wherein the CARP binds to inositol-1,4,5,-triphosphate receptor in endoplasmic reticulum in the cell.

4. A method of controlling intracellular calcium release in a cell comprising expressing a carbonic anhydrase-related protein (CARP) from an expression construct in the cell wherein the carbonic anhydrase-related protein comprises an amino acid sequence of amino acids 45 to 291 of SEQ ID NO: 2, whereby the intracellular release of calcium is controlled.

* * * * *

SEQUENCE LISTING

<160> NUMBER OF SEQ ID NOS: 14

<210> SEQ ID NO 1
<211> LENGTH: 261
<212> TYPE: PRT
<213> ORGANISM: Mus musculus

<400> SEQUENCE: 1

Gly Lys Asn Val Tyr Thr Glu Ile Lys Cys Asn Ser Leu Leu Pro Leu
 1               5                  10                  15

Asp Asp Ile Val Arg Val Val Thr His Glu Asp Cys Ile Pro Glu Val
            20                  25                  30

Lys Ile Ala Tyr Ile Asn Phe Leu Asn His Cys Tyr Val Asp Thr Glu
        35                  40                  45

Val Glu Met Lys Glu Ile Tyr Thr Ser Asn His Met Trp Lys Leu Phe
    50                  55                  60

Glu Asn Phe Leu Val Asp Ile Cys Arg Ala Cys Asn Asn Thr Ser Asp
65                  70                  75                  80

Arg Lys His Ala Asp Ser Ile Leu Glu Lys Tyr Val Thr Glu Ile Val

```
                    85                  90                  95
Met Ser Ile Val Thr Thr Phe Phe Ser Ser Pro Phe Ser Asp Gln Ser
                100                 105                 110

Thr Thr Leu Gln Thr Arg Gln Pro Val Phe Val Gln Leu Leu Gln Gly
            115                 120                 125

Val Phe Arg Val Tyr His Cys Asn Trp Leu Met Pro Ser Gln Lys Ala
        130                 135                 140

Ser Val Glu Ser Cys Ile Arg Val Leu Ser Asp Val Ala Lys Ser Arg
145                 150                 155                 160

Ala Ile Ala Ile Pro Val Asp Leu Asp Ser Gln Val Asn Asn Leu Phe
                165                 170                 175

Leu Lys Ser His Asn Ile Val Gln Lys Thr Ala Leu Asn Trp Arg Leu
            180                 185                 190

Ser Ala Arg Asn Ala Ala Arg Arg Asp Ser Val Leu Ala Ala Ser Arg
        195                 200                 205

Asp Tyr Arg Asn Ile Ile Glu Arg Leu Gln Asp Ile Val Ser Ala Leu
    210                 215                 220

Glu Asp Arg Leu Arg Pro Leu Val Gln Ala Glu Leu Ser Val Leu Val
225                 230                 235                 240

Asp Val Leu His Arg Pro Glu Leu Leu Phe Pro Glu Asn Thr Asp Ala
                245                 250                 255

Arg Arg Lys Cys Glu
            260

<210> SEQ ID NO 2
<211> LENGTH: 291
<212> TYPE: PRT
<213> ORGANISM: Mus musculus

<400> SEQUENCE: 2

Met Ala Asp Leu Ser Phe Ile Glu Asp Ala Val Ala Phe Pro Glu Lys
 1               5                  10                  15

Glu Glu Asp Glu Glu Glu Glu Glu Glu Gly Val Glu Trp Gly Tyr
            20                  25                  30

Glu Glu Gly Val Glu Trp Gly Leu Val Phe Pro Asp Ala Asn Gly Glu
        35                  40                  45

Tyr Gln Ser Pro Ile Asn Leu Asn Ser Arg Glu Ala Arg Tyr Asp Pro
    50                  55                  60

Ser Leu Leu Asp Val Arg Leu Ser Pro Asn Tyr Val Val Cys Arg Asp
65                  70                  75                  80

Cys Glu Val Thr Asn Asp Gly His Thr Ile Gln Val Ile Leu Lys Ser
                85                  90                  95

Lys Ser Val Leu Ser Gly Gly Pro Leu Pro Gly Gly Gln Glu Phe Glu
            100                 105                 110

Leu Tyr Glu Val Arg Phe His Trp Gly Arg Glu Asn Gln Arg Gly Ser
        115                 120                 125

Glu His Thr Val Asn Phe Lys Ala Phe Pro Met Glu Leu His Leu Ile
    130                 135                 140

His Trp Asn Ser Thr Leu Phe Gly Ser Ile Asp Glu Ala Val Gly Lys
145                 150                 155                 160

Pro His Gly Ile Ala Ile Ala Leu Phe Val Gln Ile Gly Lys Glu
                165                 170                 175

His Val Gly Leu Lys Ala Val Thr Glu Ile Leu Gln Asp Ile Gln Tyr
            180                 185                 190
```

-continued

```
Lys Gly Lys Ser Lys Thr Ile Pro Cys Phe Asn Pro Asn Thr Leu Leu
        195                 200                 205

Pro Asp Pro Leu Leu Arg Asp Tyr Trp Val Tyr Glu Gly Ser Leu Thr
    210                 215                 220

Ile Pro Pro Cys Ser Glu Gly Val Thr Trp Ile Leu Phe Arg Tyr Pro
225                 230                 235                 240

Leu Thr Ile Ser Gln Met Gln Ile Glu Glu Phe Arg Arg Leu Arg Thr
                245                 250                 255

His Val Lys Gly Val Glu Leu Val Gly Cys Asp Gly Ile Leu Gly
                260                 265                 270

Asp Asn Phe Arg Pro Thr Gln Pro Leu Ser Asp Arg Val Ile Arg Ala
            275                 280                 285

Ala Phe Gln
    290

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gggaattcgg tggaggttgt gcaggcaacc agcagaatc                              39

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gggggtcgac gtgttgttac aggccctgca ga                                     32

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gggaattcgg tggaggcaag aatgtgtaca cggaga                                 36

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gggggtcgac ctcacatttc ctcctggcat c                                      31

<210> SEQ ID NO 7
<211> LENGTH: 40
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 7
gggaattcgg aggaggatcc agagactacc gaaatatcat                                40

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gggggtcgac gcttgtggaa ctagatccag gacc                                      34

<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gggaattcgg tggaggagac agaggctatg gagagaag                                  38

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gggggtcgac tccccagact ggtaatggtc a                                         31

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gggaattcgg tggaggagtg gcccagcagg aaatcaa                                   37

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gggggtcgac ggtgagcgag gatgtagatg                                           30

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Synthetic -continued

```
primer

<400> SEQUENCE: 13
gggggtcgac ccggaggagg ccttggtctt cttgg                                35

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gggggtcgac agacaggctg ggctcgaagt                                      30
```